United States Patent [19]

Tomaiuolo et al.

[11] Patent Number: 4,495,465
[45] Date of Patent: Jan. 22, 1985

[54] METHOD AND APPARATUS FOR NON-DESTRUCTIVE TESTING OF MAGNETICALLY PERMEABLE BODIES USING A FIRST FLUX TO SATURATE THE BODY AND A SECOND FLUX OPPOSING THE FIRST FLUX TO PRODUCE A MEASURABLE FLUX

[75] Inventors: Frank G. Tomaiuolo, Unionville; John G. Lang, Scarborough, both of Canada

[73] Assignee: Rotesco Inc., Scarborough, Canada

[21] Appl. No.: 373,851

[22] Filed: May 3, 1982

[51] Int. Cl.³ .................... G01N 27/72; G01R 33/12
[52] U.S. Cl. .................................... 324/232; 324/239
[58] Field of Search ................. 324/239–243, 324/253–255, 262, 232

[56] References Cited

U.S. PATENT DOCUMENTS

| 2,010,813 | 8/1935 | Dysart | 324/232 |
| 2,938,163 | 5/1960 | Roffman et al. | 324/232 |
| 3,444,458 | 5/1969 | Scott | 324/243 |
| 3,568,052 | 3/1971 | Anderson | 324/253 |
| 3,739,261 | 6/1973 | Renhen, Jr. | 324/232 |

FOREIGN PATENT DOCUMENTS

| 913780 | 12/1962 | United Kingdom | 324/239 |
| 2034049 | 5/1980 | United Kingdom | 324/262 |

Primary Examiner—Gerard R. Strecker
Assistant Examiner—Walter E. Snow

[57] ABSTRACT

The present invention relates to a method and apparatus for non-destructive comparative investigation of physical characteristics affecting the reluctance of different parts of a body having magnetic permeability. In accordance with the present invention a first saturating magnetic flux is induced in the body or a part thereof giving rise to a flux distribution pattern determined by the reluctance of the body or part thereof which in turn is determined by the physical character of the body or body part. A second magnetic flux is also induced generally opposing the first magnetic flux in a selected region of the flux distribution pattern, outside of the body or body part while maintaining substantial first flux saturation of the body or body part such that any resultant magnetic flux in that region is at a readily measureable flux level. Also provided is a detector for detecting along the body either variances from that flux level with the second magnetic flux being maintained substantially constant or variances of the second magnetic flux with the resultant magnetic flux being maintained substantially constant.

42 Claims, 10 Drawing Figures

METHOD AND APPARATUS FOR NON-DESTRUCTIVE TESTING OF MAGNETICALLY PERMEABLE BODIES USING A FIRST FLUX TO SATURATE THE BODY AND A SECOND FLUX OPPOSING THE FIRST FLUX TO PRODUCE A MEASURABLE FLUX

FIELD OF THE INVENTION

The present invention relates to an improved method and apparatus for the non-destructive investigation of a body having magnetic permeability, to determine the existance of any physical anomoly or variation in the condition or state from norm which affects the reluctance of the body.

BACKGROUND OF THE INVENTION

Various instruments have been used on a commercial basis to test for both loss of metallic cross-sectional area and abrupt discontinuities in different types of ferromagnetic objects such as steel wire ropes. The testing of these ropes is particularly critical where the wire ropes are used in conveyer systems such as line shaft elevators and aerial cable systems used for transporting people from one region to another. The entire conveyer system is dependent upon the strength of the rope so that if the rope is weakened through loss of metallic cross-section area due to wear, corrosion or other effects or if it is weakened through broken wires or kinks. These weaknesses and the extent to which they effect the strength of the overall rope must be determined. If the rope is unduly weak at any point along its length it is removed from the conveyer system and this can only be determined through testing. The rope should not however be removed prematurely from the system because of the substantial replacement cost of the rope. Therefore any small weaknesses which are detected but which are not initially severe enough to justify removal and replacement of the rope should be monitored over time for increased weakening.

Steel wire ropes are only one example of the types of elongated ferromagnetic objects that should be subjected to these tests. For example there are many applications in which steel pipes, rods etc. should be tested for weakened regions to determine whether or not replacement is necessary.

Commercial instruments which have been available to date for testing ferromagnetic objects fall into two categories. The first category includes devices used primarily for measuring changes in metallic cross-sectional area of the object and the second category includes devices primarily used for detecting abrupt discontinuities in the mechanical structure of the object. Both types of devices which provide for non-destructive testing rely upon the magnetic permeability of the structure for setting up a uni-directional magnetic flux in the object. This flux is monitored for inconsistencies in the flux pattern which are representative of either changes of the cross-sectional area or anomalies in the object. In order to provide any meaningful and identifiable results from the testing the magnetic flux in the body must be substantial and will preferably saturate the body. This however presents difficulties from the standpoint that the instruments used must be capable of monitoring at an extremely high flux level, ie the level required to substantially saturate the body.

A structure which has been used in the past for testing of ferromagnetic bodies is described in Canadian Pat. No. 1,038,037 issued to Noranda Mines Limited on Sept. 5, 1978. According to the Noranda Patent an elongated ferromagnetic body is inserted in a pair of magnetic pole pieces of a testing device and a uni-directional magnetic flux which saturates the body flows through the section of the body between the pole pieces into the testing device to form a completed magnetic circuit. The pole pieces are provided with sensors which must be capable of sensing the main field of the high level magnetic flux to search for cross-sectional area differences in the body. A radial sensor is also provided for sensing radial components of the main field which are representative of anomalies such as abrupt discontinuities along the body.

SUMMARY OF THE PRESENT INVENTION

The present invention is directed to a method and apparatus adapted to overcome difficulties encountered with the prior art structures and at the same time to simplify testing of bodies having magnetic permeability. According to the present invention, which is directed to the non-destructive comparitive investigation of physical characteristics affecting the reluctance of different parts of a body and/or different bodies having magnetic permeability, first magnetomotive force means is used to induce a first magnetic flux to at least substantially saturate the body which gives rise to a flux distribution pattern determined by the reluctance characteristics of that body. At the same time and totally in contrast to any prior art arrangements a second magnetomotive force means is used for inducing a second magnetic flux generally opposing the first magnetic flux in a selected region of the flux distribution pattern. This second opposing magnetic flux is such that any resultant magnetic flux in the region is at a readily measureable flux level with either variances from that flux level along the body while the opposing flux is maintained substantially constant or variances in the opposing flux along the body to maintain a substantially constant resultant flux being indicative of the reluctance characteristics for which the body is being investigated. Detection means for detecting these variances along the body are provided for comparison thereof.

According to the present invention it is the relatively low level resultant flux of the first and second opposing fluxes rather than the high level first flux which is monitored either directly or indirectly through the control of the second flux. In fact according to an aspect of the present invention the second flux is controlled so as to reduce the resultant flux towards zero and the amount of control is in itself indicative of these reluctance characteristics.

Furthermore the resultant magnetic flux is only investigated in a specific region of the opposing fluxes and this region may be located where there is minimal flux leakage to enhance the accuracy of the testing.

BRIEF DISCUSSION OF THE DRAWINGS

The above as well as other advantages and features of the present invention will be described in greater detail according to the preferred embodiments of the present invention in which.

Figure 1:
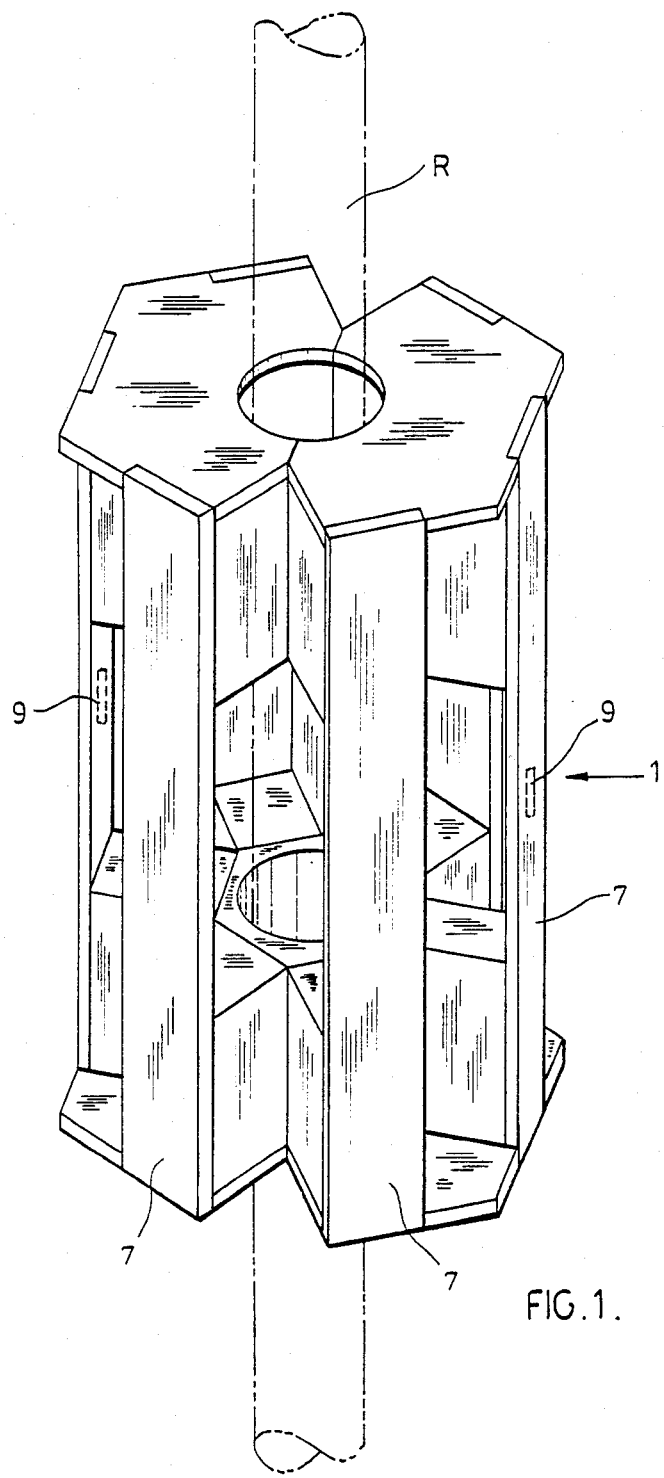
FIG. 1 is a perspective view of a testing device according to a preferred embodiment of the present invention with a portion of an elongated magnetically permeable body located in the device.

DETAILED DESCRIPTION ACCORDING TO THE PREFERRED EMBODIMENTS OF THE PRESENT INVENTION

The arrangement generally indicated at 1 in FIGS. 1 through 4 is referred to as a test head. This test head is used with a receiver console containing electronic processing circuits and a strip-chart recorder for the testing of bodies having magnetic permeability such as the steel wire rope R, shown in the figure. The purpose of the testing is to search out any cross-sectional variances in the wire rope and at the same time to locate anomolies such as broken wire strands along the rope. The test is carried out by examination of flux distribution patterns set up within the rope through the test head with variances in the pattern highlighting specific defects. In this particular arrangement the highlighting is accomplished by comparison of various parts of a common body. The testing can however be used for the testing of various different bodies in comparing the flux patterns from one body to another.

Referring again to the figures test head 1 includes a central aperture for receiving the piece to be tested. Located at either end of the test head is a pole piece 5 surrounded by a plurality of permanent magnets 3. The pole pieces and magnets are connected from one end of the test head to the other by means of a plurality of shorting bars 7 with six shorting bars being shown in the preferred embodiments of the drawings. Two opposing shorting bars are fitted with combination magnetic flux sensors and generators 9. Located interiorly of the shorting bars are a second set of combination magnetic flux sensors and generators 11. The two groups of sensors are used respectively for detecting changes in cross-sectional area of the rope and for detecting abrupt discontinuity to the mechanical structure of the rope.

As the rope is passed through the test head which, as mentioned above is electrically connected to a receiver console, the section of rope immediately within the head is magnetically saturated in a direction parallel to its axis by the strong permanent magnets 3 through the pole pieces 5 at either end of the test head.

Figure 3:
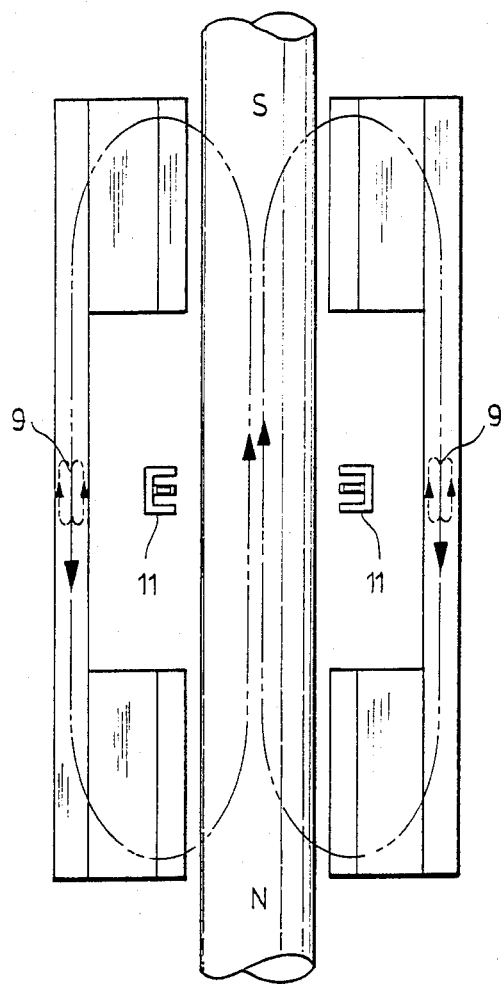
FIG. 3 is a cross-sectional view of the device of FIG. 1 showing a magnetic field as set up in the circuit formed by the body and the device.
Figure 4:
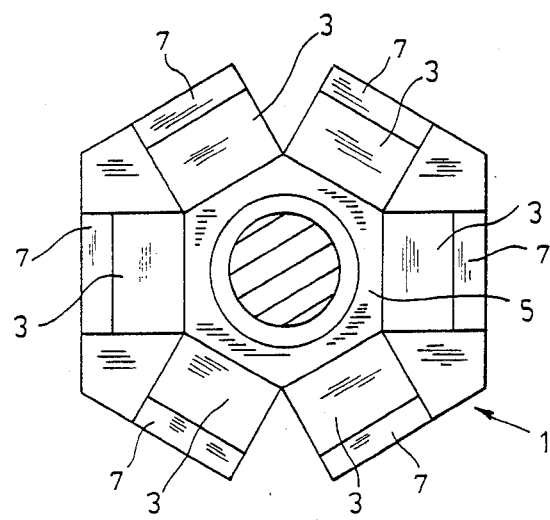
FIG. 4 is an end view of the arrangement shown in FIG. 1.

This arrangement comprising the test head which is used as a circuit forming device to form a magnetic circuit with the wire rope sets up a magnetic flux pattern as shown in FIG. 3 where the first flux flows from the north to the south end of the circuit and the opposing flux flows from south to north at the sensors 9. The amount of first flux set up in the system is known to be a function of the metallic cross-sectional area of the rope which as mentioned above, must be at least substantially magnetically saturated in the rope section at the test head. This means therefore that the first magnetic flux set up by the permanent magnets is at a very high level and if one were to use a prior art technique in determining cross-sectional area changes, one would monitor this first flux set up in the rope section which may be at such a high level as to result in non-linear measurements and therefore be difficult to work with. However, in accordance with the present invention there are no measurements taken of this first magnetic flux but rather, combination sensors and magnetic generators 9 set up the second magnetic flux in the region of the shorting bars where these generators are located with this second opposing flux outside of the wire rope opposing the first magnetic flux in that region. This produces a resultant flux which is much lower than the first magnetic flux exterior to the body and which is at a readily measureable flux level while as can be understood from FIG. 3, the wire rope itself remains substantially saturated with the first flux.

From this point the monitoring of the metallic cross-sectional area of the rope may be accomplished in either one of two ways. Firstly, the second magnetic flux may be controlled so as to substantially maintain the resultant flux at a particular readily measureable flux level and any variances of the second magnetic flux along the wire as it is passed through the test head would indicate changes in the cross-sectional area of the rope. These variances would be visually recorded on the strip chart recorder.

In a preferred arrangement using a variable second magnetic flux the resultant flux is driven towards zero and the amount of second magnetic flux required to substantially maintain the resultant flux near zero is indicative of a cross-sectional area of the wire rope. Physical characteristics which would affect the reluctance of the rope would appear as variations in the amount of second flux as the body passes through the test head.

A second method of searching out cross-sectional area changes within the rope is accomplished by providing the second flux at a level to produce a very low resultant flux with that second flux being maintained substantially constant at that level. In this arrangement the resultant flux would be monitored directly and any changes in that resultant flux along the body are indicative of cross-sectional area changes.

According to both of the embodiments described above, the monitoring or sensing is carried out within the test head by means of units 9 referred to as main field sensors. It will be seen that these sensors which as described above also include secondary flux generators are located directly within the magnetic circuits set up in the rope in the test head. Furthermore by placing the sensors in the shorting bars away from the pole pieces, much of the flux leakage occurring directly at the pole pieces and providing non-linear properties has been eliminated from the recordings in the sensor region.

Figure 5:
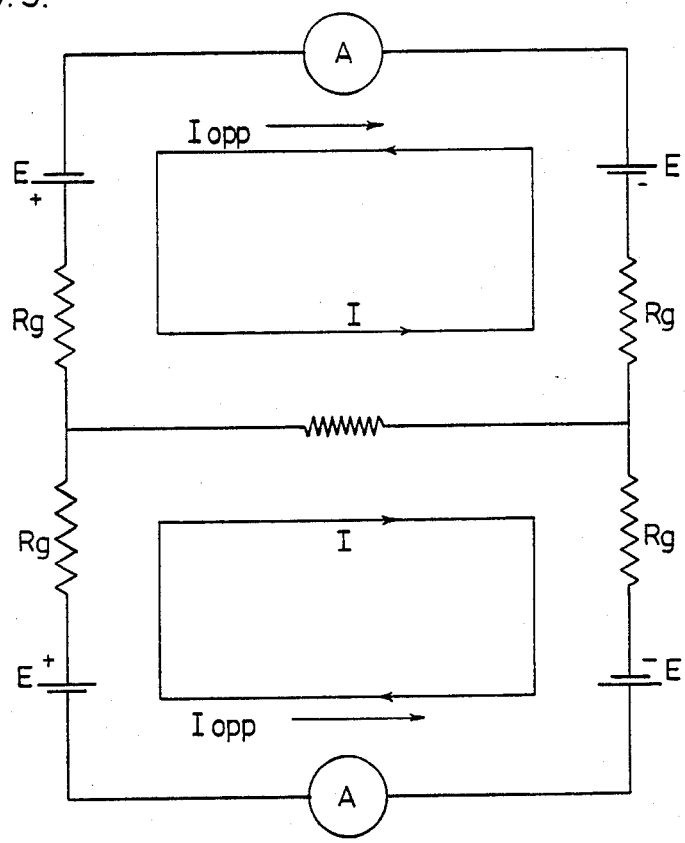
FIG. 5 is a schematic view of a circuit formed with the arrangement of FIG. 3.

The magnetic circuit of FIG. 3 is analagous to an electrical circuit as shown in FIG. 5. The magnets of the test head are represented by the batteries with the magnetomotive force generator being represented by voltages in FIG. 5. The magnetic flux is represented by the current I which flows in the same direction through the central load resistor representative of the rope itself.

The return path for the current represents the shorting bars with resistors RG representing the air gap reluctances around the pole pieces and the rope. The opposing current is Iopp, representative of the second magnetic flux and the ammeters A represent the main field sensors for sensing flux variances in the shorting bars where there is a resultant flux of the first and second opposing magnetic fluxes.

With the circuit as different loads are placed on the electrical circuit the amount of current drawn from the system can be measured on the ammeter. The reading from the ammeter will therefore indicate as the rope passes through the circuit whether or not the specific section of rope in the circuit has a constant cross-sectional area.

Figure 6:
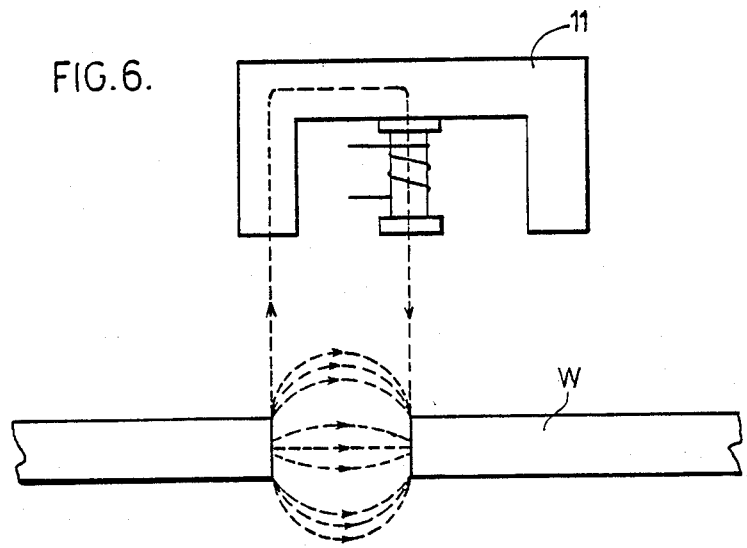
FIG. 6 is an enlarged plan view of a radial field flux pattern and a sensing device for sensing that radial field pattern as found in the arrangement of FIG. 3.

The other type of rope characteristic which produces reluctance changes in the rope and which is of prime concern is the existence of abrupt discontinuities such as broken wires in the rope. These discontinuities cause a dipole field or radial bulging of the flux pattern at the broken wire, as shown in FIG. 6 where wire W which would be typical of a wire found in the wire rope is broken. This flux pattern which is produced through the magnetic saturation of the rope section is again at a very high flux level. However, consistent with the main field sensors described above, the radial sensors are set up to induce a second magnetic flux in opposition to the first magnetic flux to arrive at a resultant magnetic flux of a readily measureable flux level. Since these particular sensors are searching for radial components of the flux distribution pattern, the opposing flux set up by the radial field sensors is substantially perpendicular to the opposing flux set up by the main field sensors. It should be noted that for clarity sake, FIG. 6 shows the low level resultant flux as sensed by the radial field sensors. As with the main field sensors these radial field sensors can be set up to operate in either one of two modes; i.e., to sense variances in the resultant flux with the second flux being maintained substantially constant or to sense variances in the second flux required to maintain the resultant flux substantially constant.

The radial field sensing arrangement is set up to detect radial flux leakages regardless of where it occurs within the cross-sectional area of the rope. Therefore, the radial field sensing assembly is constructed to substantially surround the rope and consists of two circular disks of high permeable material separated by a space parallel to the axis of the rope. A sub assembly for housing the sensors themselves is provided between these disks and this sub assembly consists of an inner ring of high permeability material and a concentric outer ring of the same material. These two rings are magnetically connected by the radial sensors.

With this arrangement any flux lines which leak across the metal-air-metal boundary follow the lower reluctance path of the assembly and since the sensors are themselves part of this low reluctance path, they are situated for monitoring of the resultant flux and for determining its polarity.

The receiver console contains electronic circuitry comprising a transmitting section for energizing elements 9 and 11 and the receiver section which processes the resultant signals picked up during sensing before presenting these signals in proper format to the recorder. This receiver section includes two channels the first of which contains the information pertinent to the main field. The circuits in this channel process the information received from the main field sensors for presentation to the recorder in a proper format. The recorder trace is then used to determine directly the changes in cross-sectional area measured in the rope.

The second channel processes the signals from the radial field sensor and presents this information to the second recorder channel. This trace is used to determine directly the location of localized anomalies in the rope.

Figure 7:
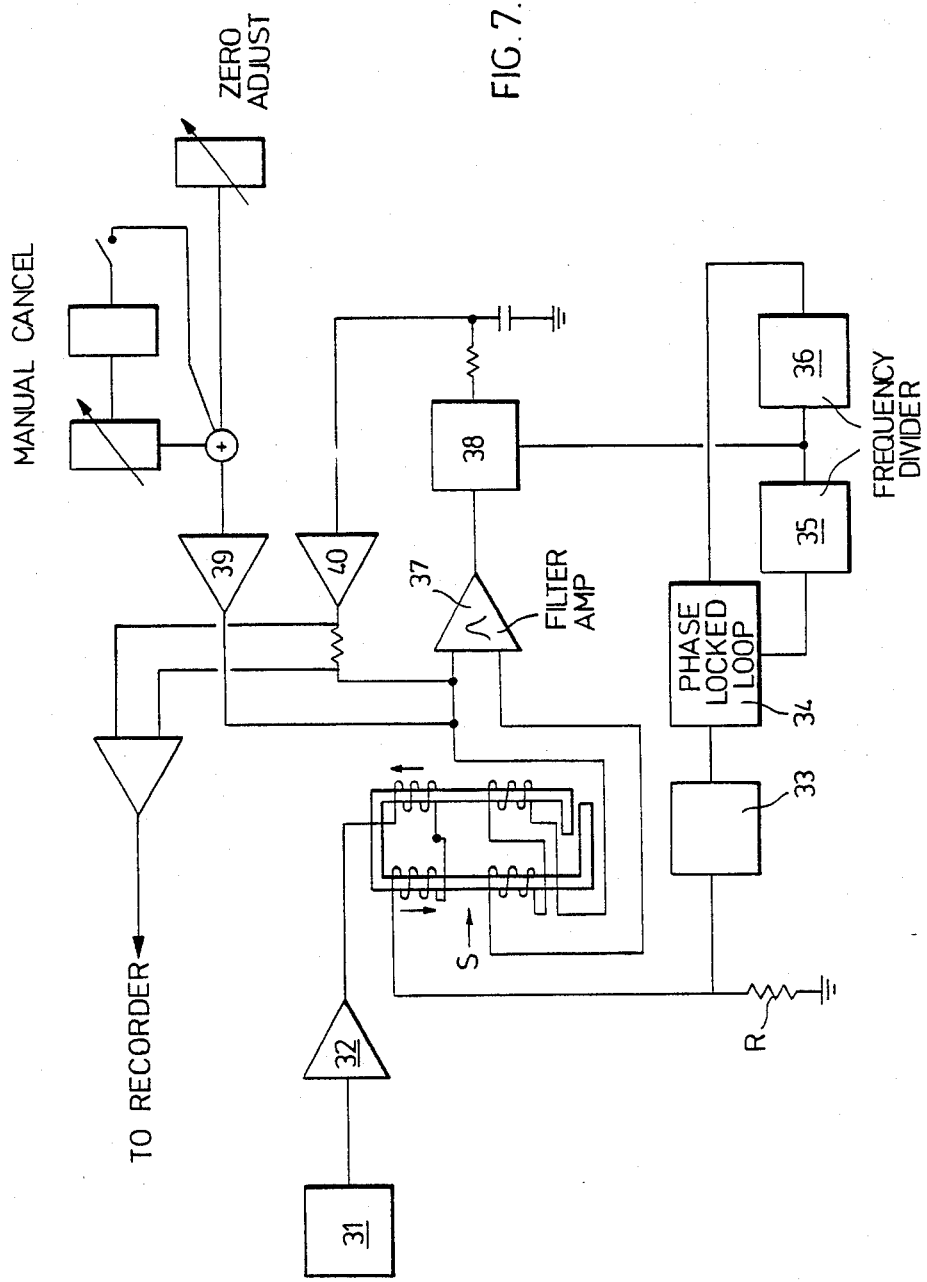
FIGS. 7 through 9 are schematic views of various circuit arrangements for the sensing of flux patterns according to various different preferred embodiments of the present invention.
Figure 8:
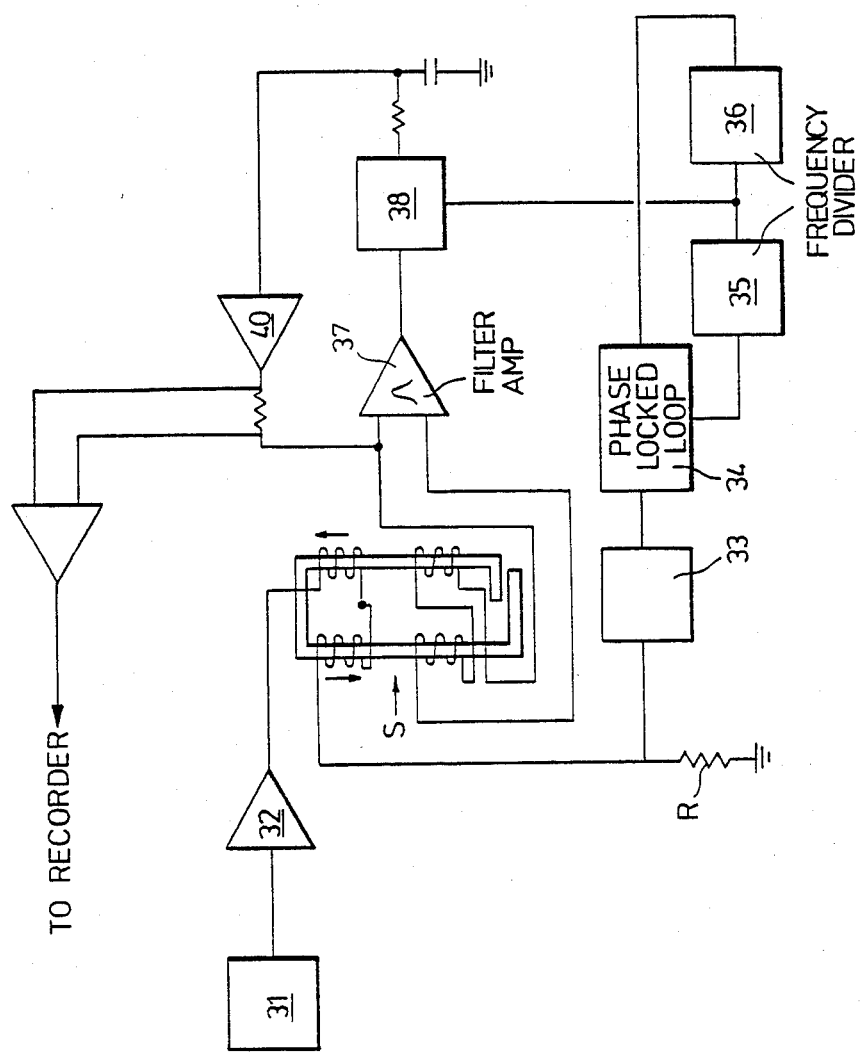
Figure 9:
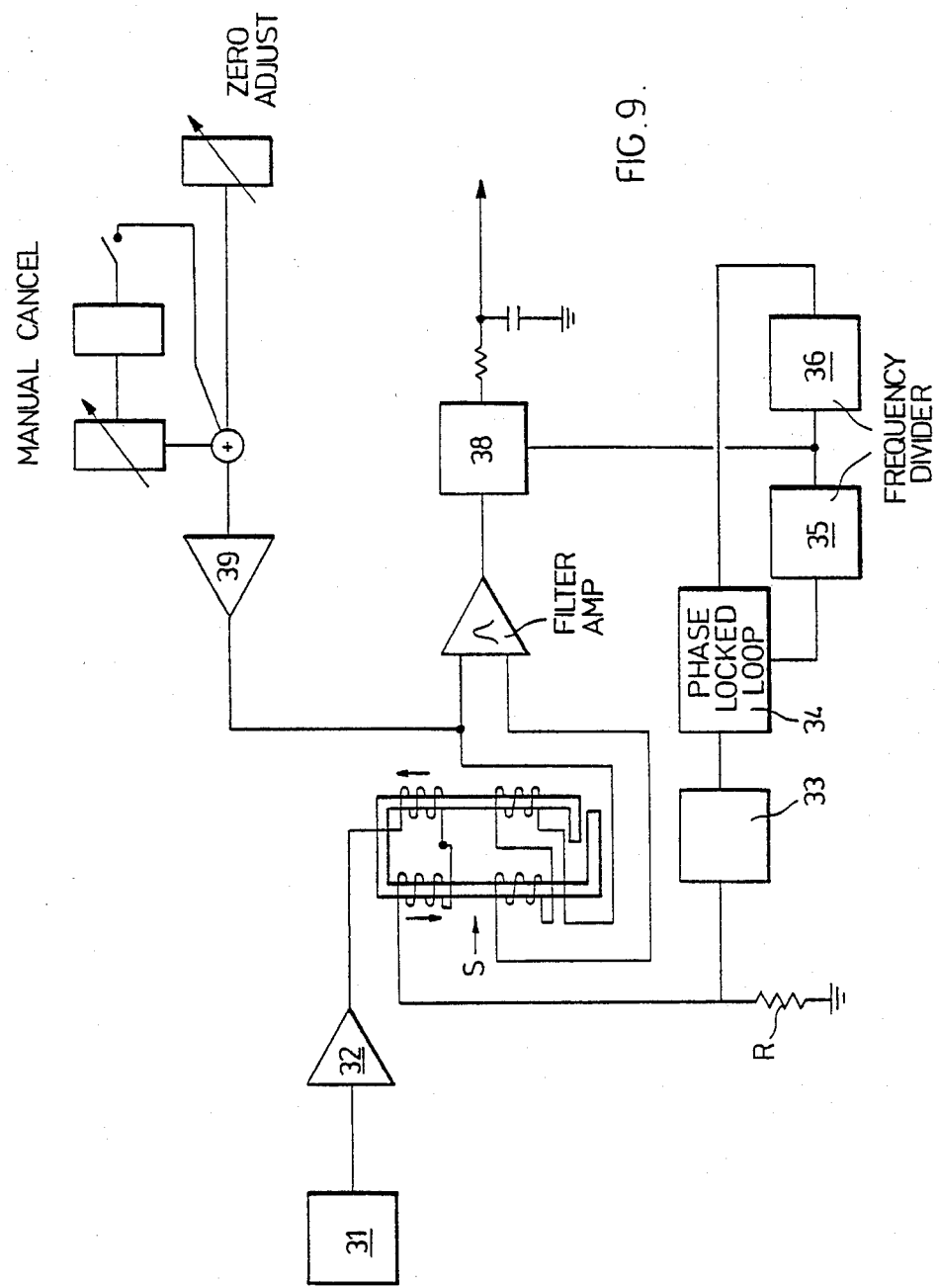

A circuit for the operation of combination sensor and flux generator 9 is shown in FIG. 7 while a circuit for the operation of combination sensor and flux generator 11 is shown in FIG. 8. These are both preferred circuit arrangements in which the second opposing magnetic flux is used to drive the resultant magnetic flux towards zero. FIG. 9 on the otherhand shows a further preferred embodiment circuit in which the second magnetic flux is maintained substantially constant.

Referring to FIG. 7 for the operation of the main field sensors an oscillator 31 feeds a current pump 32 with a sine wave of for example one kilohertz. The output of 32 is a sinosoidal current which is fed to the primary winding of the sensor consisting of two cores of high permeability material arranged as shown at S in FIG. 7. These are arranged to set up a magnetic field within the cores in accordance with the right hand rule. The drive current or voltage is of such a magnitude as to drive the coil positive and negative by equal amounts. The two cores of high permeability material should have low magnetic saturation characteristics so that they may easily be driven into saturation. The flux in the cores themselves may not swing positive or negative by these same equal amounts since this is dependant upon the external field acting on the sensor. The external field corresponds to the first magnetic flux in a selected region of the flux distribution pattern set up by the permanent magnet.

As the flux swings positive and negative it induces voltages in the secondary windings wound about the tow rores. If however an external field is applied which will usually be in the direction of the axis of the core, it biases the core unsymmetrically. The driving wave form will cause the cores to enter saturation in one direction to a greater degree than the other. The time average at the induced voltage in the second winding is indicative of the field acting on the sensor. In particular, harmonics are generated in the secondary windings and the greatest of these harmonics is the second harmonic which is proportional to the field acting on the sensor and which is emitted by the secondary windings of the sensors. This signal is amplified and filtered by filter 37 and fed to phase detector 38.

A reference voltage is obtained across the reference resistor R1. As such it is a direct measure of the current flowing in the primary winding of the sensor. A signal is then applied to a phase shifter 33 to correct for any unwanted phase shift in the circuitry. This is a manual adjustment performed when the instrument is calibrated. This output of the phase shifter is applied to a phase locked loop 34 whose output is four times the frequency or in this case 4 kilohertz. This output is divided by four in two stages by frequency dividers 35 and 36. After the first division the resulting output of two kilohertz is used to operate phase detector 38 located in the signal channel.

The output of the phase detector is filtered to yield a DC voltage which is proportional to the magnetic field applied to the sensor. The filtered output of 38 phase detector 38 is then applied to current pump 40 which in turn feeds the secondary windings of the sensor with a current which sets up a magnetic field in opposition to the applied field. The resultant flux in turn causes a voltage to be developed at the output of the phase detector which in turn affects the opposing field in the sensor. As such the system operates in a zero seeking or negative feedback mode. Therefore the amount of signal required for substantial cancellation of the resultant flux is a direct measure of the applied field and can be fed through the recorder and then metered for observation.

A zero adjustment is provided to cancel out the effects of flux leakage which occur with no rope in the system and with the test head clamped closed. This flux leakage results in an output from the sensor and phase detector 38. Therefore by inserting a signal via current pump 39 into the sensor the output of detector 38 is brought to zero.

A manual zero control is provided to cancel out the effects of the rope itself which when inserted in the test head increases its flux level. This manual zero control manually cancels this flux to once again bring the output of phase detector 38 to zero. The amount of signal available at the wiper of this control is therefore a measure of the total flux in the system attributed to the presence of the rope.

The radial sensor circuitry as shown in FIG. 8 is substantially the same as the circuitry described above with respect to FIG. 7 with the exception that the calibration circuitry comprising the manual cancel and the zero adjust are eliminated from the circuits.

The circuitry of FIG. 9 is again somewhat similar to the arrangement of FIG. 7 except that the feedback control for varying the level of the opposing flux has been eliminated. This particular circuit can be used to operate either of the sensors and preferably the radial sensor when that sensor is used for sensing variances of the resultant magnetic flux rather than changes in the second magnetic flux to maintain the resultant flux at a constant level. The output of the phase detector is fed to the recorder and metered for observation.

The specific circuits for the combination sensors and flux generators described above can of course be replaced with other types of flux sensors and/or flux generators. In this particular application the two units are designed in a single region of the shorting bar. This combination unit is preferably mounted by means of a low heat conducting material such as epoxy which provides a heat sinc to protect the sensor from the high level currents generated in the region in order to arrive at the low level resultant magnetic flux. This particular sensing arrangement is extremely durable and is relatively insensitive to temperature changes which further increases the accuracy of recordings made by the sensors.

It is of course also practical to use separate sensors and flux generators in separate regions of the circuit forming device. For example, in a situation where the opposing flux is maintained substantially constant, small permanent magnets can be mounted directly in the shorting bars and arranged to oppose the flux set up by permanent magnets 3. A separate sensing device analogous to the ammeter described above would then be located in a region of the opposing fluxes where the resultant flux is at a relatively low level to monitor this resultant flux. The proximity of the sensor and the magnets in the shorting bar would depend upon the strength of these particular magnets.

Figure 2:
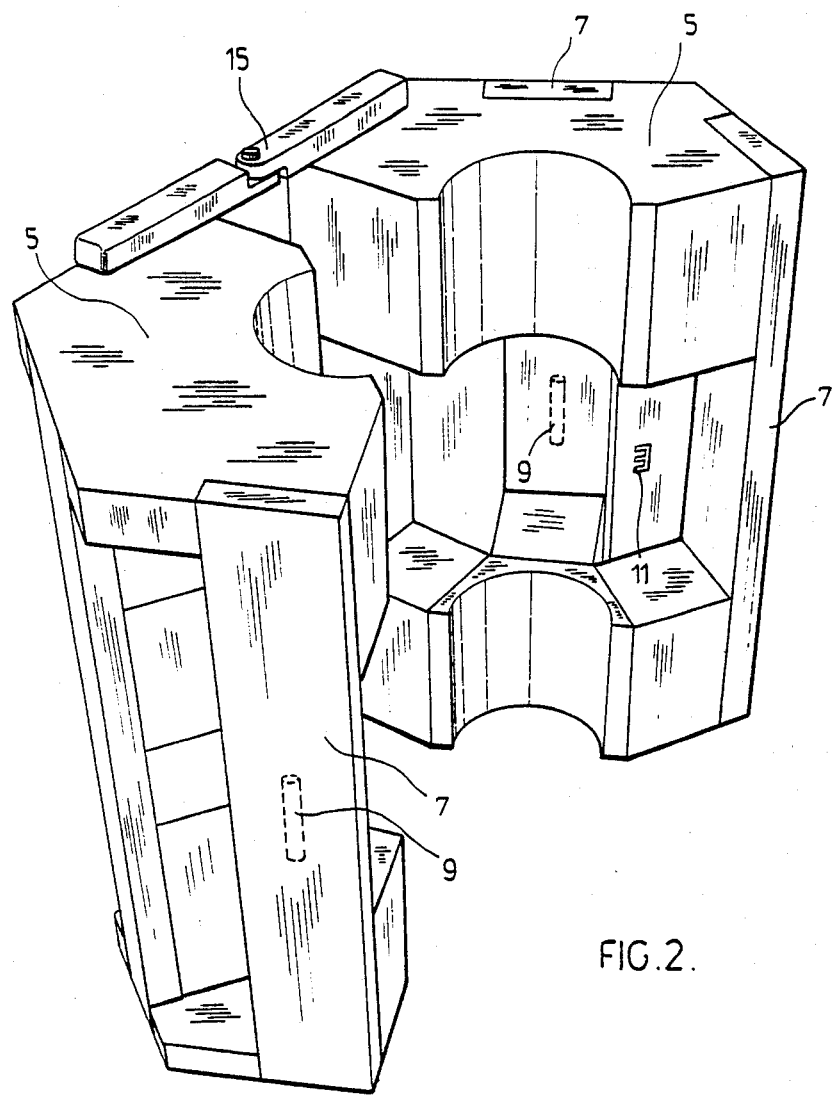
FIG. 2 is a perspective view of the device shown in FIG. 1 when open for receiving the body.
Figure 10:
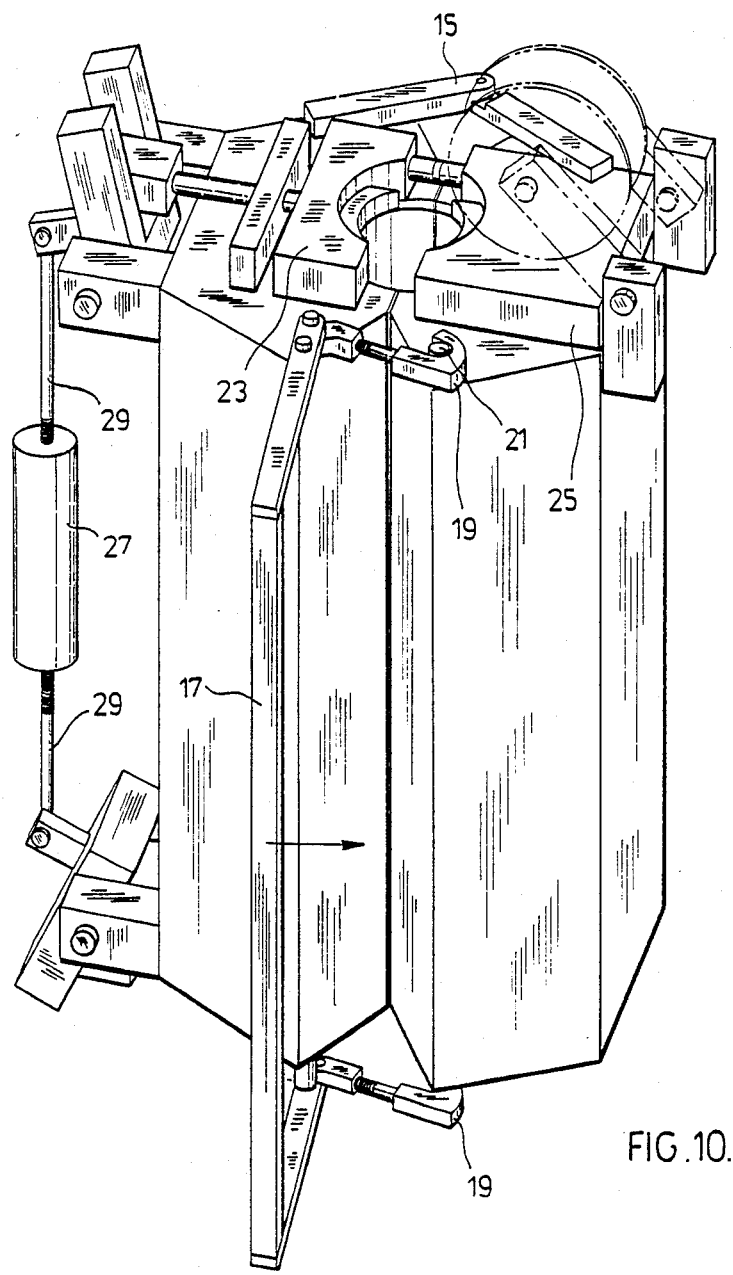
FIG. 10 is a detailed perspective view of a testing device including both closure and adjustment mechanisms according to preferred embodiments of the present invention.

Returning again to the test head itself and in particular to FIGS. 2 and 10, the head is designed with a hinge arrangement indicated at 15 to permit opening of the head for receiving the rope. The opening and closing of the hinge is controlled through a lever and hook mechanism on the opposing side of the test head from the hinge and comprising lever 17 and hooks 19. These hooks are adapted to releasably engage pins 21 and the lever is arranged to allow movement of the hooks away from the pins for opening of the test head and to clamp the hooks firmly over the pins for closing of the test head through a swinging action of the lever.

As will be appreciated, the openings to the interior of the test head must be large enough to receive a relatively large wire and must at the same time be capable of snugly accommodating a smaller wire to sit substantially centrally of the test head. Accordingly the test head is provided with a centering mechanism comprising collar portions 23 and 25 with collar portions 23 being adjustable towards and away from the fixed collar portions 25. This collar arrangement is found at both ends of the test head and the adjustment is made through a common adjustment member 27 threaded at either end to a pair of rods 29. The rods are threaded in opposite directions into the common adjustment member such that a single threading action will simultaneously and equally adjust each of the adjustable collar portions. In practice the collar portions are initially adjusted to snugly fit the wire rope and then backed off to allow the wire rope to be passed through the test head. In this manner the rope is centered with respect to all of the sensing mechanisms within the test head.

This particular embodiment of the present invention employing the six outer cover shorting bars and magnet arrangement at each end of the unit provides a very efficient magnetization of the wire rope while at the same time being relatively light in weight. The structure including the securing and centering mechanisms is furthermore uncomplicated from an operation standpoint and therefore extremely suitable for use in the field.

Although various preferred embodiments of the present invention have been described herein in detail it will be appreciated by those skilled in the art that variations may be made thereto without departing from the spirit of the invention or the scope of the appended claims.

The embodiments of the invention in which an exclusive property or privilege is claimed are defined as follows:

1. Apparatus for determining cross sectional area changes of a body part having magnetic permeability, said apparatus comprising a first magnetomotive force means for inducing a first magnetic flux to at least substantially saturate the body part giving rise to a flux distribution pattern determined by cross sectional area characteristics of the body part, a second magnetomotive force means for inducing a second magnetic flux generally opposing the first magnetic flux in a selected region of said flux distribution pattern outside of the body part such that any resultant magnetic flux in the selected region is at a readily measurable flux level while the body itself is maintained substantially saturated with the first flux and detecting means to monitor the flux in the selected region for detecting flux level variances indicative of such cross sectional area changes by comparative investigation along the body part.

2. Apparatus as claimed in claim 1, including feedback control means of said second magnetomotive force means for controlling magnitude of the second magnetic flux to reduce the resultant magnetic flux towards the readily measurable flux level, the amount of control from said feedback control means being indicative of such the magnitude of cross sectional area changes.

3. Apparatus as claimed in claim 2 wherein said feedback control means controls the magnitude of the second magnetic flux such that the resultant magnetic flux is reduced towards zero.

4. Apparatus as claimed in claim 1 wherein said apparatus includes circuit forming means for forming a magnetic circuit with the body, said first and second magnetomotive force means and said detection means being located in said circuit forming means.

5. Apparatus as claimed in claim 4 wherein said second magnetomotive force means and said detection means are located proximate one another in said apparatus.

6. Apparatus as claimed in claim 1 wherein said first magnetomotive force means magnetically saturates the body.

7. Apparatus as claimed in claim 4 wherein said circuit forming means comprises first and second pole pieces for directing the first magnetic flux into the body and shorting means having low reluctance interconnecting said first and second pole pieces.

8. Apparatus as claimed in claim 7 wherein said first magnetomotive force means comprises at least one permanent magnet in said circuit forming means.

9. Apparatus as claimed in claim 7 wherein said second magnetomotive force means and detection means are located in said shorting means.

10. Apparatus as claimed in claim 1 wherein said second magnetomotive force means comprises an electromagnetic source.

11. Apparatus as claimed in claim 10 wherein said electromagnetic source comprises a solenoid winding through which a current is passed.

12. Apparatus as claimed in claim 1 wherein said detection means comprises a first solenoid winding through which an alternating current is passed and a second winding in which a voltage is induced.

13. Apparatus as claimed in claim 4 wherein said detection means and said feedback control means are located in a region of said circuit forming means having relatively low magnetic saturation characteristics.

14. Apparatus as claimed in claim 12 wherein said second solenoid winding forms said second magnetomotive force means and including energizing means for energizing said second solenoid winding.

15. Apparatus as claimed in claim 14 wherein said first and second solenoid windings are wound around a ferromagnetic material having relatively low magnetic saturation characteristics.

16. Apparatus as claimed in claim 1 for investigating anomolies of the body, said apparatus forming a magnetic circuit with the body where the anomolies are indicated by flux leakages from the circuit, said second magnetomotive force means and detection means being located outside of the circuit for detecting such flux leakages.

17. Apparatus as claimed in claim 1 wherein said second magnetomotive force means induces a substantially constant second magnetic flux opposing the first magnetic flux.

18. Apparatus as claimed in claim 4 including controls for cancelling effects of first magnetic flux leakage from said circuit forming means.

19. Apparatus as claimed in claim 9 wherein said shorting means comprises a plurality of shorting bars arranged to substantially surround the body part.

20. Apparatus as claimed in claim 19 including 6 shorting bars located symmetrically around said circuit forming means with detectors in two opposing ones of said shorting bars.

21. Apparatus as claimed in claim 20 wherein the body has an elongated cylindrical shape and including means for centering the body interiorly of said shorting bars.

22. Apparatus as claimed in claim 21 wherein said means for centering the body comprises an adjustable collar arrangement for accomodating bodies of different diameters.

23. Apparatus as claimed in claim 19 wherein said circuit forming means comprises an elongated frame longitudinally hinged between said shorting bars and including a hook and pivotal lever mechanism for opening and closing said frame.

24. Apparatus as claimed in claim 22 wherein said circuit forming means comprises a hinged frame and wherein said adjustable collar arrangement comprises an adjustable collar portion at each end of said frame and a common adjustment member for simultaneous and equal adjustment of each collar portion.

25. Apparatus as claimed in claims 1, 2 or 3 including electronic processing circuits for processing detected variances and a recorder for visibly recording the variances detected by said detection means.

26. Apparatus as claimed in claim 5 including pole pieces and a shorting bar therebetween, said second magnetomotive force means and said detection means being mounted together with one another in a cavity of said shorting bar.

27. Apparatus as claimed in claim 26 including a material of low heat conductance for mounting of said second magnetomotive force means and said detection means in said cavity, said material acting as a heat sink for heat generated by said first magnetic flux in said shorting bar.

28. A method for determining cross sectional area changes of a body part having magnetic permeability, said method comprising inducing a first magnetic flux to at least substantially saturate the body part giving rise to a flux distribution pattern determined by cross sectional area characteristics of the body part, inducing a second magnetic flux generally opposing the first magnetic flux in a selected region of said flux distribution pattern outside of the body part such that any resultant magnetic flux in the selected region is at a readily measurable flux level while the body part itself remains substantially saturated with the first flux, and monitoring the selected region to detect flux level variances indicative of such cross sectional area changes by comparative investigation along the body part.

29. A method as claimed in claim 28, including controlling magnitude of the second magnetic flux to reduce the resultant magnetic flux towards the readily measurable flux level, the amount of control of said second magnetic flux being indicative of magnitude of the cross sectional area changes.

30. A method as claimed in claim 29 wherein the magnitude of the second magnetic flux is controlled such that the resultant magnetic flux is reduced towards zero.

31. A method as claimed in claim 28, wherein said second magnetic flux is electromagnetically induced.

32. A method as claimed in claim 28 when used for investigating anomolies of the body, where the anomolies are indicated by flux leakages from the body and including detecting these flux leakages.

33. A method as claimed in claims 28 or 32, including maintaining the second magnetic flux substantially constant.

34. A method as claimed in claim 28, including detecting the variances from different positions around the body.

35. A method as claimed in claim 34, including centering the body with respect to these different positions.

36. A method as claimed in claim 28, including electronically processing and recording any detected variances.

37. Apparatus as claimed in claim 1 including control means for controlling said second magnetomotive force means to the second magnetic flux substantially constant.

38. Apparatus as claimed in claim 1 including control means for controlling said second magnetomotive force means to vary the second magnetic flux to maintain the resultant magnetic flux substantially constant.

39. A method as claimed in claim 28 further comprising maintaining the second magnetic flux substantially constant and detecting variances in the resultant magnetic flux.

40. A method as claimed in claim 28 and further comprising varying the second magnetic flux so as to maintain the resultant magnetic flux substantially constant and detecting variances in the second magnetic flux.

41. Apparatus as claimed in claim 1 when said first magnetic flux has a high intensity flow region from said first magnetomotive force means into the body part and wherein said detecting means is located away from such high intensity flow region for detecting in a region of decreased first magnetic flux intensity.

42. A method as claimed in claim 28 wherein said first magnetic flux has a high intensity flow region from said first magnetomotive force means into the body part and wherein said second magnetic flux is induced in the selected region away from such high intensity flow region for detecting flux level variances in a region of decreased first flux intensity.

* * * * *